United States Patent [19]

Clemons et al.

[11] Patent Number: 4,474,975

[45] Date of Patent: Oct. 2, 1984

[54] PROCESS FOR PRODUCING TRIS (N-METHYLAMINO) METHYLSILANE

[75] Inventors: Johnny M. Clemons, Trinity; Benjamin G. Penn; Frank E. Ledbetter, III, both of Huntsville, all of Ala.

[73] Assignee: The United States of America as represented by the Administrator of the National Aeronautics and Space Administration, Washington, D.C.

[21] Appl. No.: 492,963

[22] Filed: May 9, 1983

[51] Int. Cl.$^3$ .............................. C07F 7/08; C07F 7/10
[52] U.S. Cl. .................................................... 556/410
[58] Field of Search ........................................ 556/410

[56] References Cited

U.S. PATENT DOCUMENTS

| | | | |
|---|---|---|---|
| 2,429,883 | 10/1947 | Johannson | 556/410 |
| 2,579,417 | 12/1951 | Cheronis | 556/410 X |
| 2,807,635 | 9/1957 | Breederveld et al. | 556/410 |
| 3,481,964 | 12/1969 | Ismail et al. | 556/410 |

FOREIGN PATENT DOCUMENTS 2834027 2/1980 Fed. Rep. of Germany ...... 556/410

*Primary Examiner*—Paul F. Shaver
*Attorney, Agent, or Firm*—Joseph H. Beumer; John R. Manning; Leon D. Wofford, Jr.

[57] ABSTRACT

A method of producing tris (N-methylamine) methylsilane, including the steps of forming and cooling a liquid solution of methylamine in an inert solvent and under an inert atmosphere at a temperature of about $-30°$ C. and slowly adding a quantity of methyltrichlorosilane while maintaining said temperature. The reaction mixture is then heated for about 60 minutes at a temperature of about 40° C., followed by filtering the solid portion from the liquid portion. The liquid is distilled to remove the solvent, resulting in a high yield of tris (N-methylamine) methylsilane.

7 Claims, No Drawings

PROCESS FOR PRODUCING TRIS (N-METHYLAMINO) METHYLSILANE

ORIGIN OF THE INVENTION

The invention described herein was made by employees of the United States Government and may be manufactured and used by or for the Government of the United States for governmental purposes without the payment of any royalties thereon or therefor.

FIELD OF THE INVENTION

This invention relates to an improved process for producing tris (N-methylamino) methylsilane, which in turn may be used to produce silicon carbide-silicon nitride fibers having desirable properties.

BACKGROUND OF THE INVENTION

Recent concern about the safety of carbon fibers has led to a program to develop silicon carbide-silicon nitride fibers, generally of the formula $Si_xN_yC_z$. Current use of carbon fibers as reinforcement in composite materials has been suggested to be potentially unsafe due to the high electrical conductivity of carbon. $Si_xN_yC_z$ fibers are $10^6$ times more electrically resistive than carbon fibers, and at the same time have similar mechanical properties. $Si_xN_yC_z$ fibers are produced from the monomer tris (N-methylamino) methylsilane, which for convenience is referred to as TNMAMS.

The preparation of TNMAMS is disclosed in German Patent Disclosure No. 2,218,960, dated Nov. 8, 1973, in which Dr. Wolfgang Verbeek is listed as the inventor. In Verbeek, a process for producing materials from homogeneous mixtures of silicon carbide and silicon nitride is disclosed. The reaction between methyltrichlorosilane and methylamine is disclosed as an example of the general reaction of converting halogen substituted silanes with one or more compounds having $NH_2$ or NH groups. Example 1 of Verbeek teaches the addition of methylamine to a solution of methyltrichlorosilane dissolved in petroleum ether for reaction at 40° C. After purification by distillation, the product is used to manufacture a resin. Example 2 teaches the use of another silane to which is added methylamine for reaction at 40° C., with purification in the same manner. Verbeek is silent about the yield of monomer.

Aliphatic chlorosilanes are also reacted with large excesses of gaseous ammonia in U.S. Pat. No. 2,579,416, to N. D. Cheronis, under anhydrous conditions. Additionally, U.S. Pat. No. 2,579,417, also to Cheronis discloses the use of a gaseous primary amine, in excess, in a similar reaction. Reaction temperatures for both Cheronis references are between −10° C. and −15° C. In U.S. Pat. No. 4,255,549 to Christophliemke et al, a reaction of methyltrichlorosilane with a great excess of ammonia is taught, where the reaction is accomplished at above 0° C. under pressure. Christophliemke et al is stated to be an improvement on the Cheronis work. Other patents teach the reaction of organohalosilane at temperatures above 0° C., such as Johannson, U.S. Pat. No. 2,429,883; Breedervald et al, U.S. Pat. No. 2,807,635; Takamizawa et al, U.S. Pat. No. 3,927,057; and Berger et al, U.S. Pat. No. 3,700,716.

Efforts to produce a significant quantity of TNMAMS which is suitable for use in the production of useful resins has not been possible using the methods described in the prior art. Several of these references teach the production of laboratory quantities of polymerizable monomers, but none provide a process which can produce large quantities of monomer of high yield and suitable purity. Scale-up of these prior art methods leads to substantial difficulties such as poor yields, difficult purification, loss of reactants and wasted by-products.

DISCLOSURE OF THE INVENTION

It is an object of this invention to provide a method of producing tris (N-methylamino) methylsilane in sufficiently high yield to justify and permit large scale production.

Another object is to provide a process for producing TNMAMS without loss of starting materials and by-products, to thereby have an economically acceptable process.

These and other objects of this invention will become apparent from a reading of the detailed description contained hereinafter.

DETAILED DESCRIPTION OF THE INVENTION

It has now been discovered that the above and other objects of this invention may be accomplished in the following manner. Specifically it has been discovered that TNMAMS may be produced in satisfactory yield without loss of starting reactants or by-products in a manner which can be scaled up to acceptable quantities of production to permit commercial use of TNMAMS.

The first step in the method of this invention is to form a solution of methylamine in an inert solvent, at a temperature of less than −20° C. Any inert solvent which remains liquid at the operating temperatures of this method is acceptable. Particularly preferred are those organic solvents which can be maintained substantially free from water contamination, since water does enter into competing reactions which adversely affect the instant method. Most preferred is petroleum ether, and particularly petroleum ether which has been dehydrated or dried. As stated above, the reaction mixture is cooled to below −20° C. and preferably to as low as −50° C. Most preferred is a temperature of about −30° C.

After the liquid solution is prepared and cooled, a suitable quantity of dry methyltrichlorosilane is added preferably while maintaining the low temperature to prevent vaporization of the methylamine. The rate of addition should be slow enough to keep the temperature below −20° C. and preferably below or about −30° C. during the entire time of addition. Rapid addition of the halosilane could result in rapid production of the by-product hydrochloric acid, which will react with the TNMAMS being produced. With slow addition, the excess liquid methylamine reacts with the hydrochloric acid being produced, to form an insoluble salt.

After the reaction mixture has been formed, cooling is stopped and heat is applied to raise the temperature to from about 35° C. to about 48° C. It is held at this temperature for from as little as 15 minutes to as long as 75 minutes. The preferred refulx temperature is about 40° C. which is preferably maintained for about 60 minutes.

After the heating step, the reaction mixture is filtered to remove the solids which have formed. Most of these solids are salts which have formed from reaction between hydrochloric acid as it is formed, and methylamine, although some salt is formed if the hydrochloric acid has the opportunity to react with the TNMAMS being produced.

Finally, the liquid portion remaining after filtration, containing wash solvents if appropriate, is distilled to remove the solvents to obtain a clear liquid at room temperature which is the desired TNMAMS.

As has been disclosed above, the reaction to produce TNMAMS of this invention is adversely affected by the presence of water or water vapor. Care should be taken to employ substantially dry reactants, and it is preferred that the entire reaction be carried out in a dry inert atmosphere. Any of the normal inert gasses may be used, such as argon or the like, but nitrogen is quite suitable and preferred from a convenience and cost standpoint.

The resulting product may be used in the production of various fibers, such as by total reflux distillation at 520° C. for about 3 hours.

EXAMPLES

The following examples are presented to illustrate the preferred embodiment of this invention. They are not intended nor should it be inferred that they limit the scope of the invention as claimed.

EXAMPLE I

A first operation of the method of this invention was performed in the laboratory.

A 3 liter three-necked flask was fitted with a nitrogen inlet, a condenser, and a dropping funnel. To the flask was added 1500 ml. of dry petroleum ether. The temperature was then lowered to −30° C. and liquified monomethylamine (150 g., 5 moles) was added to the reaction vessel to form a liquid solution. While stirring and maintaining a dry nitrogen atmosphere, methyltrichlorosilane (75 g., 0.5 mole) was added to the flask dropwise to form a reaction mixture. The reaction vessel was then modified with a Friedrich's condenser fitted with a drying tube. The other two necks of the flask were sealed with glass stoppers while maintaining the dry nitrogen atmosphere. The entire reaction apparatus was then transferred to a hood and the reaction mixture heated at 40° C. for one hour. The contents of the flask were then filtered through a medium fritted glass filter into a 3 liter three-necked flask to remove solids while maintaining a dry inert atmosphere. The flask containing the filtrate was fitted with distillation apparatus and tris (N-methylamino) methylsilane was collected at 149°–151° C. The product was a clear liquid at room temperature. Quantities of this TNMAMS was polymerized to form a useful polycarbosilizane resin.

EXAMPLE II

A large scale operation of the method of this invention was then performed to demonstrate the suitability for commercial quantity production.

A 22.5 liter three neck flask was placed in section, fitted with a stirrer and calcium chloride drying tube and filled with 13 liter of petroleum ether. A temperature bath constructed from a 30 gallon container and having 40 feet of ½ inch diameter coiled copper tubing placed therein was filled with 15 gallons of ethanol and cooled to −30° C. in one hour by passing liquid nitrogen through the copper coil placed in the bath.

The system was then purged with nitrogen and 6 liters of methylamine was allowed to condense into the cold petroleum ether. This was done by passing a line from the amine gas tank first through the liquid nitrogen-cooled ethanol contained in the bath and then into the cold petroleum ether.

After addition of the amine to the petroleum ether to form a liquid solution, a dropping funnel containing methyltrichlorosilane (900 ml., 1150 g) was installed into one of the necks of the flask. The methyltrichlorosilane was slowly added with stirring to form a reaction mixture. Upon completion, the dropping funnel was replaced with a Friedrich's condenser equipped with a calcium chloride drying tube. The temperature was maintained at −30° C.

The liquid nitrogen flow through the copper coil was stopped after the formation of the reaction mixture. After a short period where ambient air was passed through the tubing until the temperature of the reaction mixture reached 40° C. This temperature was held for one hour by alternately heating and cooling the coil with hot or cold water.

After the heating of the reaction mixture was completed, the condenser was removed and the reaction flask connected to a filtration system as herein described. Adequate care was taken to insure that the glass tubing vessel did not contact the salt produced by the reaction.

The filtration operation is accomplished by the establishment of a pressure differential in the system that causes the reaction mixture to flow from the reaction pot, through the filtration device, and into a 22.5 liter three neck filtration flask. The pressure differential was established by connecting the filtration pot to a water aspirator.

Glass tubing inserted through a rubber stopper was placed into one of the necks of the filtration flask and connected to the water aspirator with rubber tubing. Next a calcium chloride drying tube and stopcock was fitted into the connection between the filtration flask and water aspirator.

Flow of the reaction mixture from the reaction vessel into the filtration flask was accomplished by starting the water aspirator. The rate of flow was regulated by opening and closing the stopcock. This operation was stopped once the petroleum ether level was barely above the surface of the salt. The stopcock was then closed and dry air pumped into the system.

After attaining atmospheric pressure in the reaction pot, the port through which the air had been pumped was opened and a dry nitrogen inlet line was quickly installed in the opening. A funnel was also placed in the opening with the dry nitrogen line, and about six liters dry petroleum ether was poured through the funnel into the reaction pot. The stirrer was then activated for five minutes to rinse product from the salt. The salt was allowed to settle to the pot bottom after stopping the stirrer and the filtration device.

After the filtration operation was completed, the filtration pot contained about 14 liters of ether-product solution which was completely salt free. At this point, the filtration device and water aspirator connections were both removed from the outside port of the filtration pot. One pot was plugged with a glass stopper and the other with a drying tube under nitrogen.

The pot containing the ether-product solution was then connected to a distillation apparatus.

After making the proper connections and installations, the water aspirator was started. About 500 ml of ether-product solution was allowed to flow into the distillation pot by opening the stopcock located between the petroleum ether-product containing vessel and distillation pot. The water aspirator remained on as a heating mantel was placed under the distillation flask. The heating was started and the stopcock between the ether-product pot and distillation pot adjusted to allow solution to trickle into the distillation pot at about the rate which the condensate was collected in the recovery pot.

The distillation operation was continued until less than 100 mls of ether-product remained in the filtration pot. At this time, the heating mantel was turned off and removed from the distillation pot. The water aspirator remained on until the temperature of the vapors was 40° C. Then the isolation valve between the recovery pot and aspirator was closed. Shortly afterward the vacuum system connection to the recovery pot was replaced by a drying tube.

The solution in the pot was now highly concentrated in product and extreme care was exercised to prevent moisture from entering the system at any time.

Although the distillation pot solution was mostly product containing a little dissolved ether, small amounts of other impurities such as side reaction products were also present. Therefore further purification of the product was necessary.

To begin the purification operation, the previously removed heating mantel was placed around the distillation pot and turned on. This distillation proceeded at laboratory atmospheric pressure, not under a vacuum as in the previous distillation operation.

Shortly after the vapor temperature reached 146° C., the heating mantel was turned off and removed from the distillation pot. When the distillation pot temperature reached 50° C., the recovery pots were removed while a dry nitrogen stream was purging the distillation system. One port of a clean, flame dried, 1 liter -3 port distillation pot was immediately connected to the take-off and the other two ports were plugged with drying tubes.

The heating mantel was again placed around the distillation pot and turned on. The temperature of the vapors quickly reached 146° C. and the product was collected until the temperature began to increase. Immediately, when the temperature moved above 146° C., the heating mantel was turned off and removed from the distillation pot.

In this particular experiment, 673 mls of the product TNMAMS were recovered. Material remaining after the 146° C. distillation separation was considered impurities and discarded after the product pot was removed from the system. Yield was calculated to be approximately 58.6% by weight.

Infra-red spectra of tris (N-methylamino) methylsilane were taken using a Perkin-Elmer 137 Sodium Chloride Spectrophotometer. The liquid monomer was placed in sodium chloride cells under anhydrous conditions.

NMR spectra were prepared using a Varian EM-300 system with deuterated chloroform as the solvent and tetramethylsilane as an external reference.

A Waters Associated HPLC with 46 K injector and Model 440 UV absorbance detector was used for chromatographic analysis. The weight percentage of tris (N-methylamino) methylsilane in the final product mixture was estimated by comparison of the areas under the peaks of the chromatogram using the cutting and weighing technique. The product was polymerized to yield a useful polycarbosilizane resin.

The above example is merely illustrative and is not to be construed as limiting the scope of our invention, which is limited only as indicated by the appended claims.

We claim:

1. In the method of producing tris (N-methylamino) methyl silane which comprises reacting methyltrichlorosilane with methylamine in an organic solvent by heating a reaction mixture thereof and purifying the resulting product by distillation, the improvement comprising:
    (a) forming said reaction mixture by preparing a liquid solution of methyl amine in said solvent at a temperature of less than −20° C. and slowly admixing in said solution a quantity of methyltrichorosilane while maintaining said temperature and
    (b) filtering the reaction mixture after reacting the same and prior to distillation so as to remove insoluble by-product material.

2. The improvement of claim 1 wherein said method is carried out under a dry inert atmosphere.

3. The method of claim 2 wherein said inert atmosphere is nitrogen and said inert solvent is petroleum ether.

4. The method of claim 1 where said solution is maintained at a temperature of from about −20° C. to about −50° C.

5. The method of claim 4 wherein said temperature is about −30° C.

6. A method of producing tris (N-methylamino) methylsilane, comprising the steps of:
    (a) forming and cooling a liquid solution of methylamine in an inert atmosphere and in an inert solvent at a temperature of about −30° C.;
    (b) slowly admixing a quantity of methyltrichlorosilane to said solution while maintaining said temperature to form a reaction mixture in said inert atmosphere;
    (c) heating said reaction mixture at a temperature of about 40° C. for about 60 minutes to produce a solid portion and a liquid portion;
    (d) filtering said liquid portion from said solid portion while maintaining said inert atmosphere; and
    (e) distilling the liquid portion under pressure in said inert atmosphere to remove said solvent.

7. The method of claim 6 wherein said inert atmosphere is nitrogen and said inert solvent is petroleum ether.

* * * * *